(12) United States Patent
Fujikawa et al.

(10) Patent No.: US 8,304,601 B2
(45) Date of Patent: Nov. 6, 2012

(54) MOUSE MODEL FOR EYE DISEASE

(76) Inventors: Keiko Fujikawa, Sapporo (JP); Kaoru Inoue, Sapporo (JP)

(*) Notice: Subject to any disclaimer, the term of this patent is extended or adjusted under 35 U.S.C. 154(b) by 166 days.

(21) Appl. No.: 12/524,268

(22) PCT Filed: Jan. 23, 2008

(86) PCT No.: PCT/JP2008/000069
§ 371 (c)(1),
(2), (4) Date: Jul. 23, 2009

(87) PCT Pub. No.: WO2008/090742
PCT Pub. Date: Jul. 31, 2008

(65) Prior Publication Data
US 2010/0031379 A1 Feb. 4, 2010

(30) Foreign Application Priority Data
Jan. 23, 2007 (JP) ................. 2007-012458

(51) Int. Cl.
*G01N 33/00* (2006.01)
*A01K 67/027* (2006.01)
(52) U.S. Cl. ............................. 800/3; 800/18
(58) Field of Classification Search ............ 800/3, 8, 800/18
See application file for complete search history.

(56) References Cited

OTHER PUBLICATIONS

Wagner (May 1995, Clin. and Experimental Hypertension, vol. 17, pp. 593-605).*
Mullins (1996, J. Clin. Invest., vol. 98, 1557-1560).*
Wall (1996, Theriogenology, vol. 45, p. 57-68).*
Doody (Nature Immunology, Jun. 2001, vol. 2, No. 6, p. 542-547).*
Tedford (Nature Immunology, Jun. 2001, vol. 2, No. 6, p. 548-555).*
Fujikawa (J Exp Med, Nov. 17, 2003, vol. 198, No. 10, p. 1595-1608).*
Sauzeau (Nature Med, Jul. 2006, vol. 12, No. 7, p. 841-845).*
Swat (Immunologic Res. 2005, vol. 32, No. 1-3, p. 259-265).*
Fujikawa (PLoS ONE, Feb. 2010, vol. 5, No. 2, e9050, p. 1-11).*
Holsinger (Current Biol., Apr. 1998, vol. 8, No. 10, p. 563-572).*
Aihara (Invest. Ophthalmol. Vis. Sci., Apr. 2003, vol. 44, No. 4, p. 1581-1585).*
Chang (BMC Genetics, 2001, vol. 2, No. 18, p. 1-12).*
Humphries (Nature Genetics, Feb. 1997, vol. 15, p. 216-219).*
Lem (PNAS, Jan. 1999, vol. 96, p. 736-741).*
Rascher (Vision Research, 2004, vol. 44, p. 2091-2100).*
Saari (Neuron, Mar. 2001, vol. 29, p. 739-748).*
Fujikawa et al., "Vav Family Bunshi no NK Saibo deno Hataraki—NKG2D/DAP, DAP12 o Kaisuru Saibo Shogai Sayo Signaling Keiro eno Kotonatta Kan'yo", Dai 34 Kai The Japanese Society for Immunology Gakujutsu Shukai, p. 333 (2004).

(Continued)

*Primary Examiner* — Michael C. Wilson
(74) *Attorney, Agent, or Firm* — Edwards Wildman Palmer LLP; Peter F. Corless

(57) ABSTRACT

It is intended to provide an animal model which shows a naturally occurring eye disease symptom, particularly ocular hypertension and/or retinal degeneration. The invention relates to a non-human animal for eye disease model in which the function of Vav2 gene and/or Vav3 gene have/has been impaired. Because the animal shows a naturally occurring eye disease symptom, such as ocular hypertension and/or retinal degeneration without administering a drug or placing it in a special growth environment, it can be used as a model useful for elucidation of onset mechanism of eye disease or evaluation for therapeutic agent for eye disease. When it is applied for such a purpose, because it is not affected by an exogenous factor, which is conventionally administered for artificially inducing eye disease, it reflects a natural pathology, therefore, the clinical and industrial usefulness thereof is high.

5 Claims, 11 Drawing Sheets

OTHER PUBLICATIONS

Fujikawa et al., The Jounral of Experimental Medicine, 198(10):1595-1608 (2003).
Doody et al., Nature Immunology, 2(6):537-541, 543 (2001).
Aihara, Practical Ophthalmology, pp. 378-379 (2006).
Aihara, Japanese Journal of Ocular Pharmacology, 20(1):59-62 (2006).
Office Action mailed Jun. 19, 2012 in Japanese Patent Application No. 2008-555002, Fujikawa et al., filed Jul. 14, 2009.
Wells et al., "Vav1 and Vav2 Play Different Roles in Macrophage Migration and Cytoskeletal Organization", Experimental Cell Research 310:303-310 (2005).

\* cited by examiner

MOUSE MODEL FOR EYE DISEASE

TECHNICAL FIELD

The present invention relates to providing a non-human animal for eye disease model. More specifically, the present invention relates to a non-human animal for eye disease model in which the function of Vav2 gene and/or the function of Vav3 gene have/has been impaired.

BACKGROUND ART

As it has been reported that almost 80% of the information a human receives from the outside world is visual information, eyes are one of the most important sensory organs for human. Thus, although most of eye diseases may not be lethal, an eye disease which may eventually lead to loss of vision can significantly impair everyday life of a human so that a development of a therapeutic method for treating such disease is very important for human beings.

As one of the most important eye diseases that may eventually lead to loss of vision, a disease accompanied with retinal degeneration or optic nerve degeneration, which lead to loss of vision due to retinal nerve damage, can be mentioned. Such degeneration induces symptoms such as reduced visual acuity, narrowed vision field, damaged vision field, ocular circulation impairment, etc. and can eventually lead to loss of vision.

In particular, glaucoma, in which retina is impaired by elevated intraocular pressure, becomes a big problem with aging population. As such, for developing a therapy using a drug which is effective for treating an eye disease such as glaucoma, etc., establishing an animal for eye disease model which has ocular hypertension and/or retinal degeneration is a very important task to be achieved.

Until now, various types of model animals expressing symptoms of an eye disease have been prepared. Most of them are a model animal in which symptoms same as those found for an eye disease are induced by administration of a certain compound or a drug. For example, in Patent Document 1, a model animal having retinosis with damaged blood vessel of retina caused by administration of Rose-Bengal to a GK rat, i.e., an animal with congenital diabetes mellitus, is disclosed. Further, in Patent Document 2, a laboratory animal in which ocular hypertension and optic nerve damage are induced by injecting a solution containing a cross-linked polymer to an anterior chamber is disclosed. Meanwhile, according to Patent Document 3, GLAST knock-out mouse is disclosed as a model having glaucoma with normal intraocular pressure in which the function of endogenous GLAST gene is impaired, and it is one example of a model animal having symptoms of an eye disease that is caused by inhibiting a function of a certain gene.

However, for the former case which discloses a model animal having symptoms same as those found for an eye disease that are induced by administration of a certain compound or a drug, a problem has been pointed out that an issue associated with reproducibility or a question regarding whether or not a relationship between the symptoms induced and actual cause of a disease is directly reflected remain unsolved. In addition, for the latter case, the use of the GLAST knock-out mouse is limited to a model having glaucoma with normal intraocular pressure.

Patent Document 1: International Publication No. WO2004/080166 pamphlet
Patent Document 2: JP-A No. 2003-149236
Patent Document 3: International Publication No. WO2004/092371 pamphlet

DISCLOSURE OF THE INVENTION

Problems to be Solved by the Invention

An object of the present invention is to provide a model animal which shows a naturally occurring eye disease symptom, particularly ocular hypertension and/or retinal degeneration.

Means for Solving the Problems

Separate from providing an animal for eye disease model, inventors of the present invention prepared a knock-out mouse in which the function of Vav2 gene and/or the function of Vav3 gene, both are one type of Vav family gene, have/has been impaired, based on research for solving a function of an immunoresponsive reaction. Surprisingly, it was newly found that the knock-out mouse naturally shows symptoms of various eye diseases including ocular hypertension and the like, and therefore each invention of the followings was completed.

(1) Non-human animal for eye disease model in which the function of Vav2 gene and/or the function of Vav3 gene have/has been impaired.

(2) The non-human animal for eye disease model described in above (1) in which the function of Vav2 gene and the function of Vav3 gene have been impaired.

(3) The non-human animal for eye disease model described in above (1) or (2) in which the eye disease is a disease which is accompanied with at least one symptom of retinal degeneration, optic nerve degeneration, elevated intraocular pressure, ocular hypertension, reduced visual acuity, narrowed vision field, and damaged vision field.

(4) The non-human animal for eye disease model described in above (2) or (3) in which the eye disease is glaucoma.

(5) The non-human animal for eye disease model described in any of above (1) to (4) in which the non-human animal is a mouse.

(6) A method of screening a compound having an activity of treating an eye disease, including the steps of administering the compound to a non-human animal in which the function of Vav2 gene and/or the function of Vav3 gene have/has been impaired and confirming a therapeutic activity of the compound against an eye disease.

(7) The method of screening described in above (6) in which the non-human animal is a non-human animal in which the function of Vav2 gene and the function of Vav3 gene have been impaired.

(8) The method of screening described in above (6) or (7) in which the eye disease is a disease which is accompanied with retinal degeneration and the therapeutic activity of the compound is confirmed by measuring intraocular pressure.

(9) The method of screening described in above (6) or (7) in which the eye disease is a disease which is accompanied with retinal degeneration and the therapeutic activity of the compound is confirmed by pathological test of ocular tissues.

(10) The method of screening described in any of above (7) to (9) in which the eye disease is glaucoma.

(11) The method of screening described in any of above (7) to (9) in which the eye disease is any one of retinosis, macula degeneration, or macula edema.

BEST MODE FOR CARRYING OUT THE INVENTION

According to the present invention, the non-human animal in which the function of Vav2 gene and/or the function of Vav3 gene have/has been impaired means a non-human animal in which a mutation is introduced to a region which encodes the amino acid sequence for endogenous Vav2 gene and/or Vav3 gene present in chromosome, or a mutation is introduced to a region for controlling expression of the gene, for example, to a promoter region or an intron region, or whole or part of the genes is substituted with other gene, typically with an exogenous marker gene so that the function of Vav2 gene and/or the function of Vav3 gene are/is not expressed or constantly inhibited. According to the present invention, the non-human animal in which the function of Vav2 gene and/or the function of Vav3 gene have/has been impaired include both a homozygote in which two of each of the endogenous Vav2 gene and/or Vav3 gene are impaired and a heterozygote in which one of each of the endogenous Vav2 gene and/or Vav3 gene is impaired, and a homozygote non-human animal is preferably used. In addition, with respect to a type of an animal, a mouse is particularly preferred.

Vav2 and Vav3 are a kind of an oncogene which belongs to the proteins of vav family and correspond to a group of enzyme proteins which promote exchange reaction of GDP/GTP in Rho/Rac small G proteins. It was reported that Vav2 activates Rac1 or Cdc42 (Betty P. et al., Mol. Cell. Biol., 2000, Vol. 20, No. 19, pages 7160-7169) while Vav3 is involved with activation of phosphoinositide 3 kinase via Rac1 and response of a B cell receptor (Inabe et al., J. Exp. Med., 2002, Vol. 195, No. 2, pages 189-200).

Figure 2:
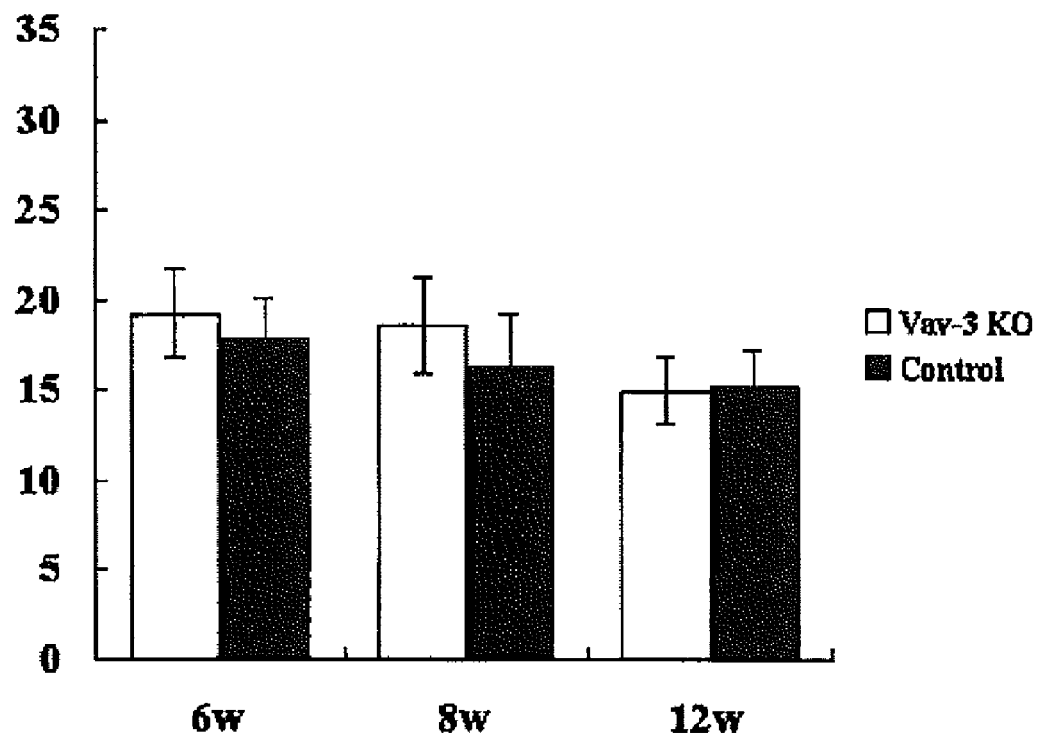
FIG. 2 shows change in intraocular pressure for a normal mouse and Vav3$^{ko}$. Vertical axis indicates intraocular pressure (mmHg), and the horizontal axis indicates the number of weeks after the animal is born.

Representative example of the non-human animal in which the function of Vav2 gene and/or the function of Vav3 gene have/has been impaired as described in the present invention is a knock-out mouse in which the function of Vav2 gene and/or the function of Vav3 gene have/has been impaired, that had been either used or produced from the study carried out by Fujikawa K. et al. (J. Exp. Med., 2003, Vol. 198, No. 10, pages 1595-1608). According to the study, a mouse in which the function of Vav2 gene has been impaired (in FIG. 2 of the document it is expressed as Vav2$^{ko}$, and the same expression is used for the present specification), a mouse in which the function of Vav3 gene has been impaired (in FIG. 2 of the document it is expressed as Vav3$^{ko}$, and the same expression is used for the present specification), a mouse in which both Vav2 gene and Vav3 gene have been knocked out while Vav1 gene is included in a normal state (in FIG. 2 of the document it is expressed as Vav2/3$^{ko}$, and the same expression is used for the present specification), and a mouse in which Vav1 gene has been also knocked out in addition to Vav2 gene and Vav3 gene (in FIG. 2 of the document it is expressed as Vav1/2/3$^{ko}$, and the same expression is used for the present specification) are used.

Production of a mouse in which the function of Vav2 gene is impaired was reported by Doody G. M. (Nature Immunology, 2001, Vol. 2, No. 6, pages 542-547). In addition, production of a Vav3$^{ko}$ mouse was reported by Fujikawa K. et al. described above (J. Exp. Med.). Vav2/3$^{ko}$ is a homo-type mouse in which the functions of Vav2 gene and Vav3 gene have been impaired, and it can be produced by a repeat breeding between Vav2$^{ko}$ and Vav3$^{ko}$. In addition, Vav1/2/3$^{ko}$ is a homo-type mouse in which all of the functions of Vav1 gene, Vav2 gene and Vav3 gene have been impaired, and it can be produced by a repeat breeding between a mouse in which Vav1 gene has been impaired and a mouse in which Vav2 gene has been impaired (Doody G. M. et al., Nature Immunology) to give a mouse in which the functions of both Vav1 gene and Vav2 gene have been impaired, and then by a further repeat breeding of the resulting mouse with Vav3$^{ko}$, based on the study carried out by Tarakhovsky A. et al. (Nature, 1995, Vol. 374, pages 467-470). Further, Vav1 gene, Vav2 gene and Vav3 gene and the nucleotide sequence thereof have been already known and registered with GenBank with accession No. NM_011691 (Vav1), accession No. NM_009500 (Vav2) and accession No. NM_020505 (Vav3), respectively.

Strains of Vav3$^{ko}$, Vav2/3$^{ko}$ and Vav1/2/3$^{ko}$ are currently all maintained by the laboratory of Dr. Frederick W. Alt at Harvard University located in Massachusetts, USA and by the laboratory of Dr. Swat W. at Washington University located in Missouri, USA and also its supply system is well established. However, these mice have not been established as a model for an eye disease and also have not been used as a non-human animal for evaluation of an eye disease. In this regard, according to the present invention, use of Vav2$^{ko}$, Vav3$^{ko}$, Vav2/3$^{ko}$ and Vav1/2/3$^{ko}$ as a non-human animal for eye disease model is provided. Herein below, when Vav2$^{ko}$, Vav3$^{ko}$, Vav2/3$^{ko}$ and Vav1/2/3$^{ko}$ are all described in together, it will be simply described as Vav2-3KO mouse.

The above described study by Fujikawa et al. is focused to determine the role played by Vav1, Vav2 and Vav3 in differentiation of immune cells in a lymphatic system, and uses a mouse in which each of Vav1, Vav2 and Vav3 gene or a combination thereof is impaired. However, no descriptions are given regarding the relationship between the Vav gene and an eye disease, and especially induction of symptoms of an eye disease by impairing Vav2 gene and/or Vav3 gene.

Surprisingly, for Vav2/3$^{ko}$, intraocular pressure starts to increase several weeks after the birth of an animal, and after 6 weeks the intraocular pressure is 40% or higher than a control mouse. In addition, from the anatomical point of view, inhibited formation of trabecular meshwork in iridocorneal angle and stenosis of Schlemm's canal are found.

Further, atrophic degeneration of retina, degeneration of lens, thickening of cornea, angiogenesis in cornea, vasodilation in an optic nerve, infiltration of neutrophils in a vitreous body, etc. are also observed. Such degenerations in cornea, iridocorneal angle, lens, vitreous body, retina, and optic nerve are clinically the findings which support reduced visual acuity, narrowed visual field, damaged visual field, retinal detachment, loss of vision, and the like. For Vav2/3$^{ko}$, since conditions gradually progress after such changes in tissues are shown, it can be widely adopted for a so-called age-related evaluation of an eye disease, without being related to glaucoma, retinosis and the like.

As it is described in the above, for Vav2/3$^{ko}$, symptoms of an eye disease, in particular a significant ocular hypertension and/or retinal degeneration, are naturally induced as the function of Vav2 gene and/or the function of Vav3 gene are/is impaired. In many cases, ocular hypertension and/or retinal degeneration are generally accompanied with a certain type of an eye disease. Examples of an eye disease which can cause ocular hypertension and/or retinal degeneration include a fundus disease, damaged visual field, open-angle glaucoma, primary closed-angle glaucoma, primary open-angle glaucoma, simple glaucoma, ocular hypertension, ocular hypotension, congenital glaucoma, traumatic glaucoma, hemorrhagic glaucoma, neovascular glaucoma, Posner Schlossman syndrome, steroidal glaucoma, Sturge Weber syndrome, plateau iris malignant glaucoma, closed-angle glaucoma due to essential iris atrophy, Chandler's syndrome, absolute glaucoma (disease of a vitreous body), physiological muscae volitantes, detachment of a posterior vitreous body, photopsia, diabetic retinopathy, retinal artery occlusion, retinal vein occlusion, macula degeneration, macula edema, retinopathy of prematurity and the like.

Accordingly, a method of screening a compound having an activity of treating an eye disease, including the steps of administering the compound to Vav2-3KO mouse of the present invention and confirming a therapeutic activity of the compound against an eye disease can lead to evaluation or search of a therapeutic agent for any of the above described diseases. Preferably, the evaluation or search of a therapeutic agent can be carried out by administering the compound to Vav2-3KO mouse of the present invention and by obtaining the reduction of intraocular pressure of the mouse or the inhibited expression of retinal degeneration, that is induced by the compound. Measurement of intraocular pressure can be conveniently carried out by using a commercially available instrument for measuring intraocular pressure, for example, Tonolab rebound tonometer (manufactured by Tiolat, Finland), an electronic voltmeter, and others. In addition, the inhibited expression of retinal degeneration can be confirmed by pathological observation of an eye ball tissue of a non-human model animal. Alternatively, by determining the appearances specific for each type of eye diseases or the expression of a marker protein or a gene, screening can be also carried out.

Specifically, Vav2/3$^{ko}$ and Vav2$^{ko}$ mice respond to a known drug compound that is currently used as a therapeutic agent for treating glaucoma for human by lowering intraocular pressure, and reduction of intraocular pressure was confirmed, as it is shown in the Examples described in detail below. Therefore, by using the Vav2/3$^{ko}$ and Vav2$^{ko}$ mice, a compound which has an activity of lowering intraocular pressure, which can be useful for treating a human, can be directly searched or evaluated.

Further, since the Vav2-3KO mouse used for the present invention exhibits symptoms of an eye disease such as ocular hypertension or retinosis, etc., due to impaired function of Vav2 gene and/or Vav3 gene, use of Vav2-3KO mouse as an animal for eye disease model allows investigation and identification of a gene or a protein involved with an eye disease of which expression is either stimulated or inhibited in relation to Vav2 gene and/or Vav3 gene. For example, a gene or a protein of which expression is either stimulated or inhibited in Vav2-3KO mouse compared to a control mouse can be investigated or identified as a gene or a protein relating to an eye disease, by using various methods such as differential display method, DNA microarray, electrophoresis, mass analysis and the like. A gene or a protein relating to an eye disease that is identified accordingly, or an onset mechanism of eye disease that is elucidated by using them may lead to possibility of providing a further progress in treating the diseases. Therefore, using the Vav2-3KO mouse as an animal for eye disease model can provide a significant contribution to a corresponding industry.

Further, although the knock-out mouse in which the function of Vav2 gene and/or the function of Vav3 gene have/has been impaired as disclosed in the above described document by Fujikawa K. et al. is a representative example of the non-human animal in which the function of Vav2 gene and/or the function of Vav3 gene have/has been impaired, as it is described in the present invention, the non-human animal used for the present invention is not limited thereto. For example, the mouse produced by Fujikawa K. et al. is a mouse of C57BL/6 strain, but a mouse of other strain that is different from C57BL/6 strain can be also used. Production of a mouse in which the function of Vav2 gene and/or the function of Vav3 gene have/has been impaired from such mouse of different strain can be carried out according to the methods that are separately described in the above documents; i.e., Doody G. M. et al. for $Vav2^{ko}$ (Nature Immunology, 2001), Fujikawa K. et al. for a mouse having impaired Vav3 (J. Exp. Med., 2003), and Tarakhovsky et al. for a mouse having impaired Vav1 (Nature, 1995 et al.). Further, there can be a case in which Vav2 gene or Vav3 gene of a different mouse strain or a non-human animal other than a mouse consists of a nucleotide sequence that is different from Vav2 gene and Vav3 gene used by Fujikawa K. et al. However, even for such case, it is still within the scope of techniques that can be easily carried out by a person skilled in the art to impair the function of Vav2 gene and/or Vav3 gene of a non-human animal, in view of the methods described in the above document by Fujikawa K. et al. (J. Exp. Med., 2003) and the document by Doody G. M. et al. (Nature Immunology, 2001) which is related to a mouse having impaired Vav1 and Vav2. Still further, impairing a function of a gene can be achieved according to a publicly known method of producing a knock-out animal, for example, by a gene targeting method.

Herein below, the present invention will be described in greater detail in view of the non-limiting examples.

EXAMPLES

Example 1

Figure 1:
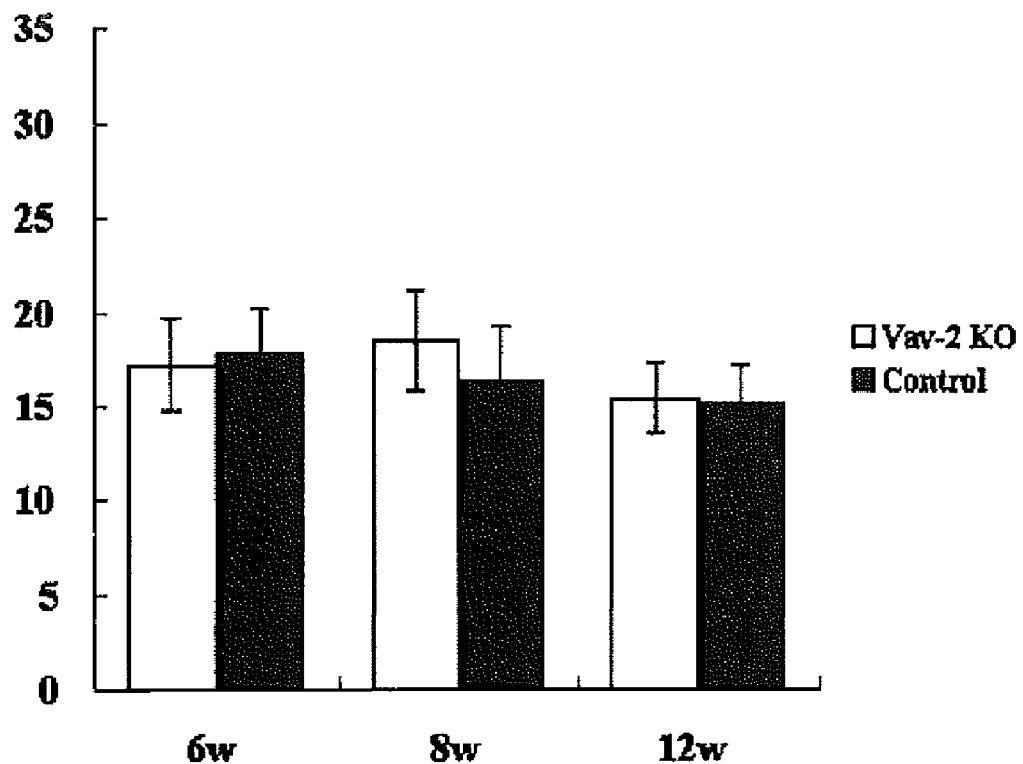
FIG. 1 shows change in intraocular pressure for a normal mouse and Vav2$^{ko}$. Vertical axis indicates intraocular pressure (mmHg), and the horizontal axis indicates the number of weeks after the animal is born.
Figure 3:
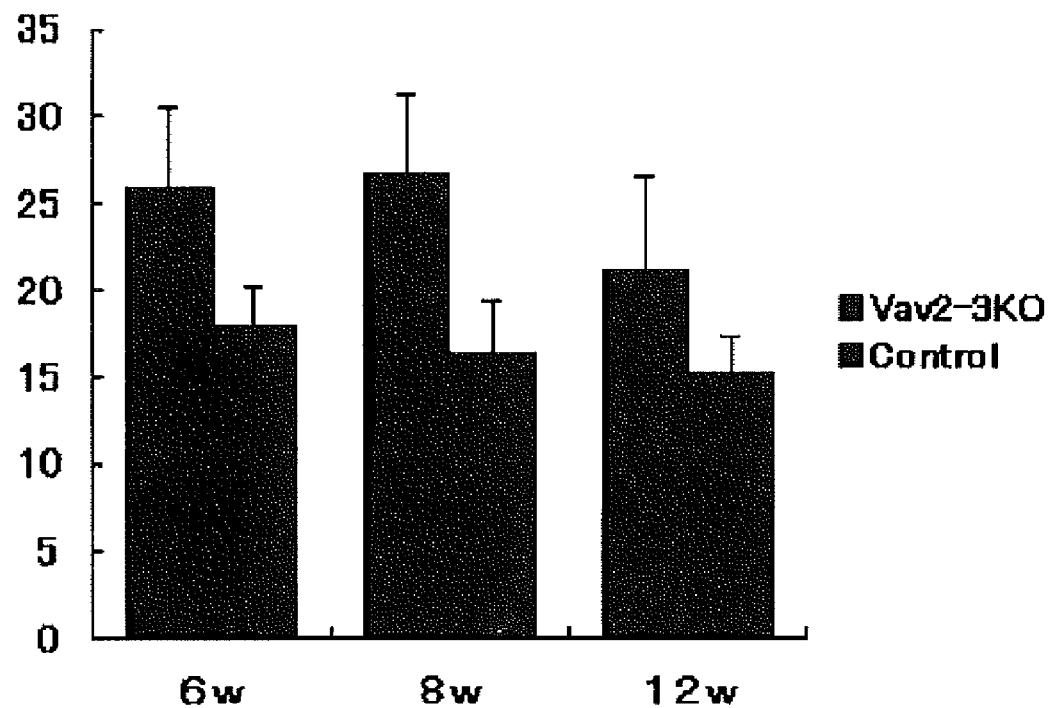
FIG. 3 shows change in intraocular pressure for a normal mouse and Vav2/3$^{ko}$. Vertical axis indicates intraocular pressure (mmHg), and the horizontal axis indicates the number of weeks after the animal is born.

$Vav2^{ko}$ obtained from Dr. Swat W.'s laboratory at Washington University and $Vav3^{ko}$ obtained from Dr. Frederick W. Alt's laboratory at Harvard University (Massachusetts, USA) were separately subjected to back-crossing into C57BL/6 mouse, and then $Vav2^{ko}$ and $Vav3^{ko}$ were bred with each other to obtain $Vav2/3^{ko}$. Four animals for each of $Vav2^{ko}$, $Vav3^{ko}$ and $Vav2/3^{ko}$ were raised under barrier free condition at SPF level designated by School of Medicine of Hokkaido University, according to the guidelines suggested by the Animal Committee. Further, using a Tonolab rebound tonometer (manufactured by Tiolat, Finland), intraocular pressure was measured every weak between 10 o'clock in the morning and noon under the condition recommended in the manual. The experiment was repeated four times using a different mouse every time, and overall sixteen animals were subjected to the experiment. The resulting data was analyzed based on two-tailed Student's t-test and standard deviation was obtained (P<0.01). Further, as a control, C57BL/6 mouse was also prepared and the intraocular pressure was measured at the same time. Results are shown in FIG. 1 ($Vav2^{ko}$), FIG. 2 ($Vav3^{ko}$) and FIG. 3 ($Vav2/3^{ko}$), respectively.

For $Vav2^{ko}$ and $Vav3^{ko}$, it was confirmed that intraocular pressure was increased by approximately 5 to 20% compared to the control.

In addition, intraocular pressure was significantly increased in $Vav2/3^{ko}$ and the intraocular pressure of 6-week old $Vav2/3^{ko}$ was increased by approximately 40% compared to the control mouse.

Example 2

From the control mouse (B6mouse) No. 22 (Table 1) and $Vav2/3^{ko}$ No. 18 (Table 2), both left and right eye balls were taken out, embedded for preservation, thinly sliced, and stained with hematoxylin-eosin (HE; Sigma) to give a pathological tissue specimen. The specimen was then examined under an optical microscope.

TABLE 1

| Group | | Wild type (B6) | |
|---|---|---|---|
| Animal Number | 1 | Right eye ball ♂ 16D | Same |
| | 2 | Left eye ball ♂ 16D | mouse |
| | 3 | Right eye ball ♂ 16D | Same |
| | 4 | Left eye ball ♂ 16D | mouse |
| | 5 | Right eye ball ♂ 4W | Same |
| | 6 | Left eye ball ♂ 4W | mouse |
| | 7 | Right eye ball ♂ 4W | Same |
| | 8 | Left eye ball ♂ 4W | mouse |
| | 9 | Right eye ball ♂ 4W | Same |
| | 10 | Left eye ball ♂ 4W | mouse |
| | 11 | Right eye ball ♂ 4W | Same |
| | 12 | Left eye ball ♂ 4W | mouse |
| | 13 | Right eye ball ♂ 9W | Same |
| | 14 | Left eye ball ♂ 9W | mouse |
| | 15 | Right eye ball ♂ 9W | Same |
| | 16 | Left eye ball ♂ 9W | mouse |
| | 17 | Right eye ball ♂ 11W | Same |
| | 18 | Left eye ball ♂ 11W | mouse |
| | 19 | Right eye ball ♂ 21W | Same |
| | 20 | Left eye ball ♂ 21W | mouse |
| | 21 | Right eye ball ♂ 21W | Same |
| | 22 | Left eye ball ♂ 21W | mouse |

TABLE 2

| Group | | $Vav2\text{-}3^{ko}$ | |
|---|---|---|---|
| | 1 | Right eye ball ♂ 20D #4 | Same |
| | 2 | Left eye ball ♂ 20D #4 | mouse |
| | 3 | Right eye ball ♂ 20D #5 | Same |
| | 4 | Left eye ball ♂ 20D #5 | mouse |
| | 5 | Right eye ball ♂ 4W #6 | |
| | 6 | Left eye ball ♂ 4W #6 | |
| | 7 | Right eye ball ♂ 4W #7 | Same |
| | 8 | Left eye ball ♂ 4W #7 | mouse |
| | 9 | Right eye ball ♂ 9W #8 | Same |
| | 10 | Left eye ball ♂ 9W #8 | mouse |
| | 11 | Right eye ball ♂ 11W #9 | Same |
| | 12 | Left eye ball ♂ 11W #9 | mouse |
| | 13 | Right eye ball ♂ 16M #10 | Same |
| | 14 | Left eye ball ♂ 16M #10 | mouse |
| | 15 | Right eye ball ♂ 26 W #11 | |
| | 16 | Left eye ball ♂ 26 W #11 | |
| | 17 | Right eye ball ♂ 26 W #12 | Same |
| | 18 | Left eye ball ♂ 26 W #12 | mouse |

Observation results were summarized according to the following grading criteria.

TABLE 3

| Grade | Stricture of scleral venous sinus | Recession of trabecular meshwork |
|---|---|---|
| − | No change | No change |
| ± | Lumen area is ⅔ or more | Slight recession |

TABLE 3-continued

| Grade | Stricture of scleral venous sinus | Recession of trabecular meshwork |
|---|---|---|
| + | Lumen area is between 1/3 and 2/3 | Weak recession |
| ++ | Lumen area is 1/3 or less | Moderate recession |
| +++ | Mostly occluded | Very significant recession |

Figure 4:
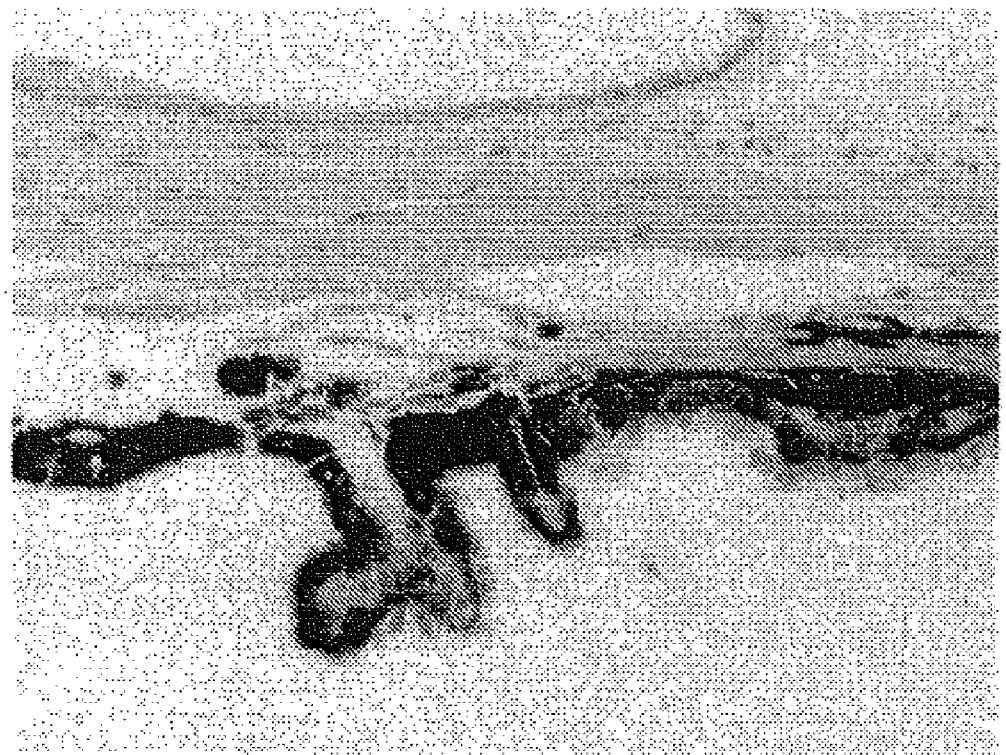
FIG. 4 is a photo image showing trabecular meshwork and Schlemm's canal of a 21-week old control mouse (i.e., B6 mouse), obtained by optical microscopic measurement.
Figure 5:
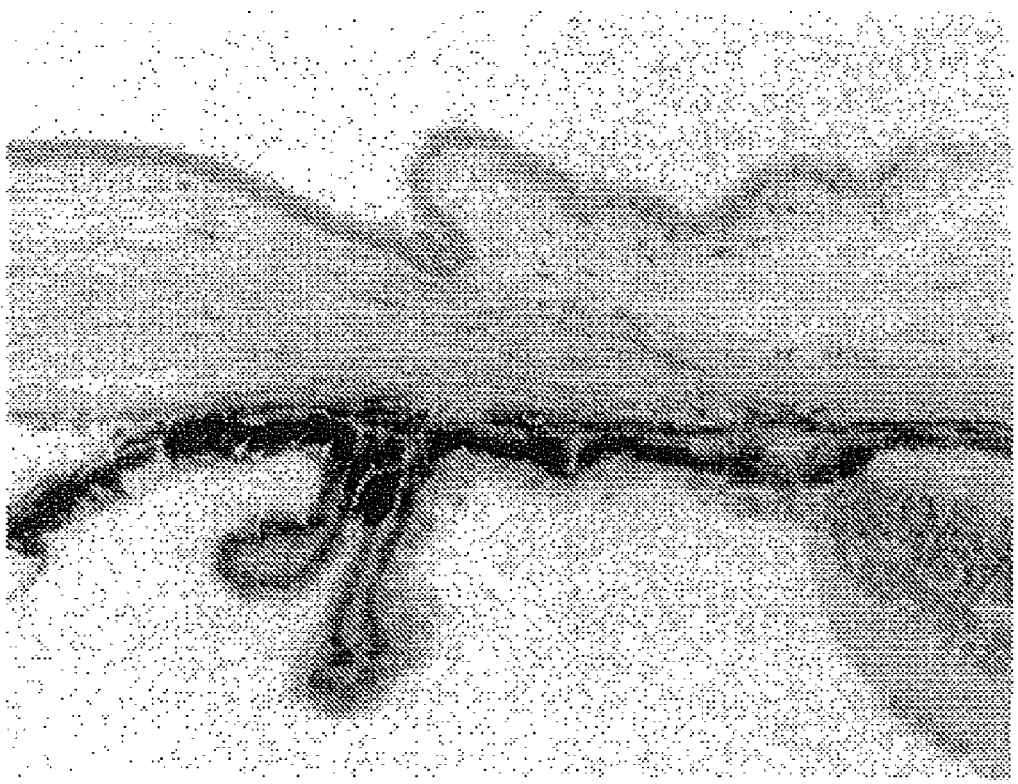
FIG. 5 is a photo image showing trabecular meshwork and scleral venous sinus of a 9-week old Vav2/3$^{ko}$ mouse, obtained by optical microscopic measurement.
Figure 6:
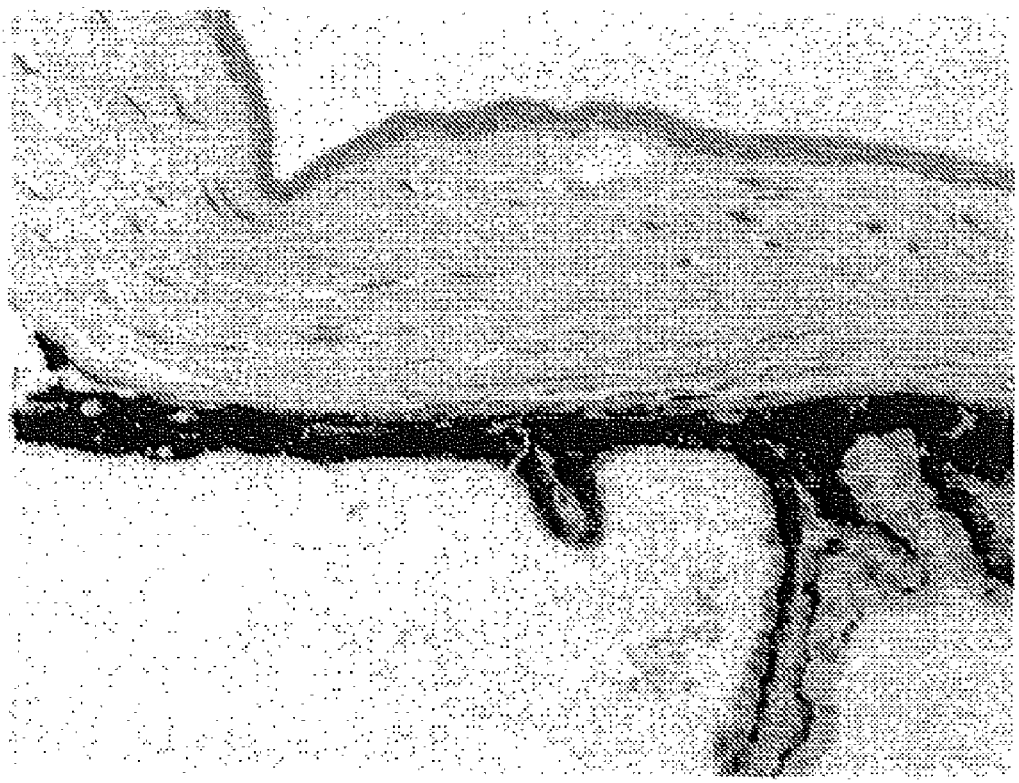
FIG. 6 is a photo image showing trabecular meshwork and scleral venous sinus of a Vav2/3$^{ko}$ mouse, obtained by optical microscopic measurement.

As a result, although a slight abnormality was found from one eye of the four eyes of Day 16 group of a control mouse, eight eyes of Week 4 group, four eyes of Week 9 group, two eyes of Week 11 group, and four eyes of Week 21 group showed no abnormalities. Photo image of a 21-week old control mouse obtained by optical microscopic measurement was given as a representative example (FIG. 4). Meanwhile, from Day 20 group and Week 4 group of Vav2/3$^{ko}$ mouse, slight, weak or moderate stricture of scleral venous sinus and recession of trabecular meshwork were found. From Week 9 group to Week 26 group, very significant stricture of scleral venous sinus and recession of trabecular meshwork were found. Among them, as a representative example, FIG. 5 shows moderate stricture of scleral venous sinus and recession of trabecular meshwork and FIG. 6 shows very significant stricture of scleral venous sinus and recession of trabecular meshwork.

Figure 7:
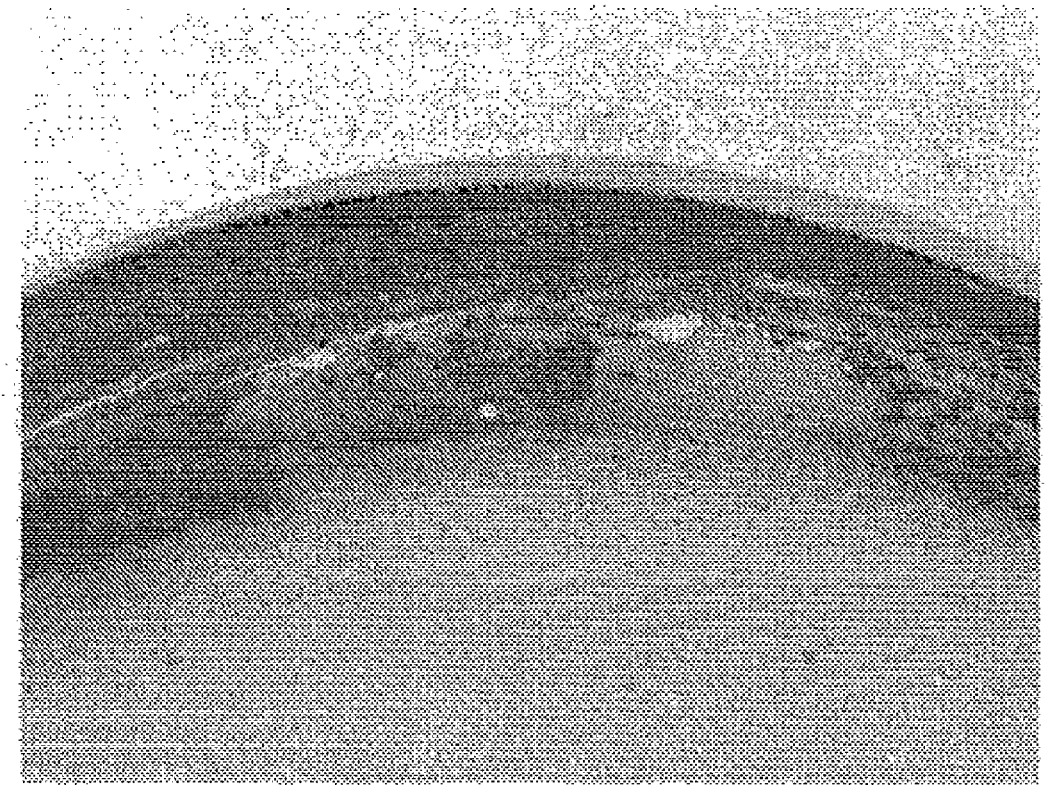
FIG. 7 is a photo image showing lens degeneration found in Vav2/3$^{ko}$ mouse.
Figure 8:
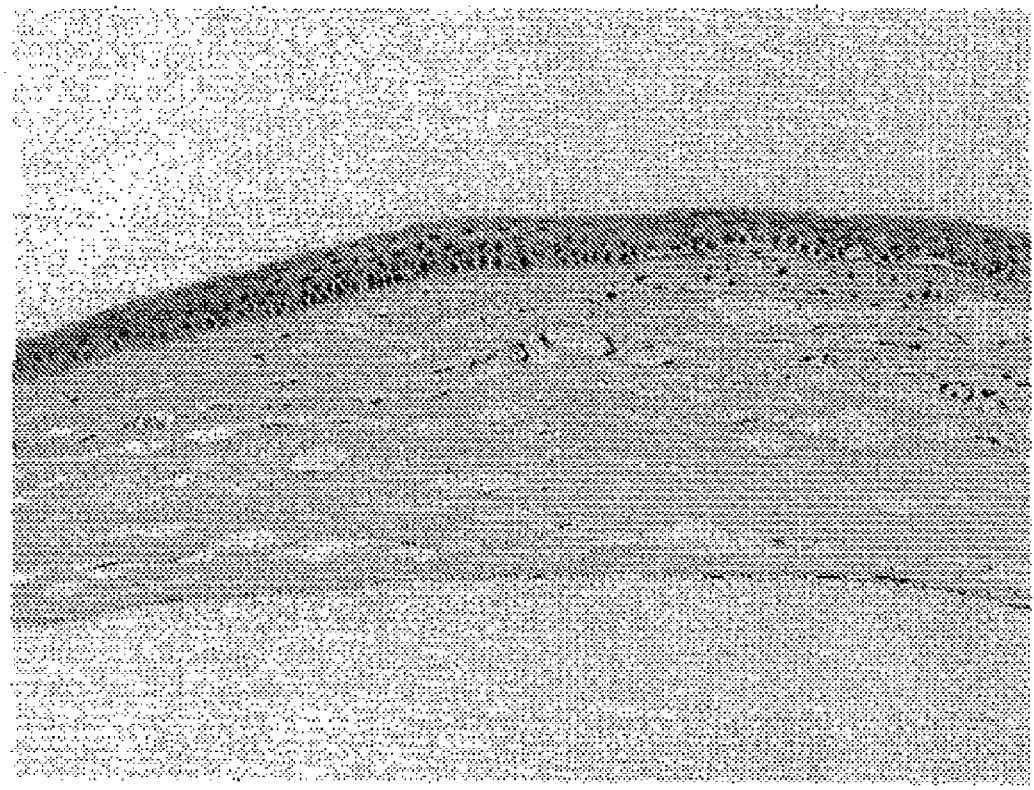
FIG. 8 is a photo image showing cornea thickening and angiogenesis found in Vav2/3$^{ko}$ mouse.
Figure 9:
FIG. 9 is a photo image showing vasodilation of an optic nerve found in Vav2/3$^{ko}$ mouse.
Figure 10:
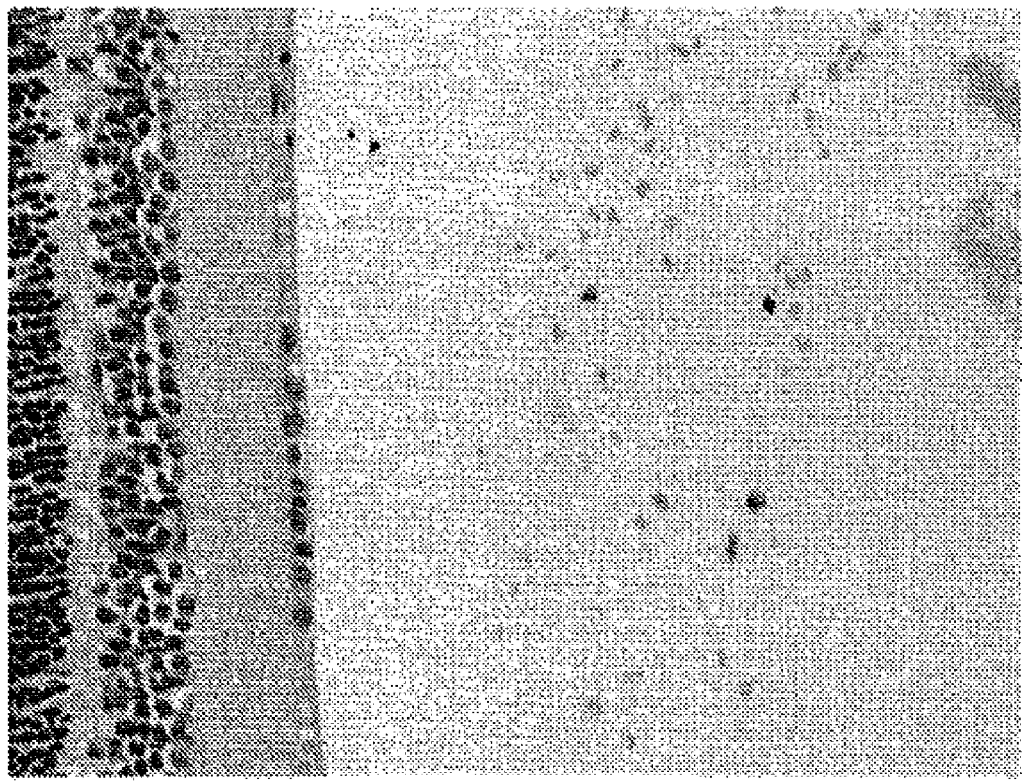
FIG. 10 is a photo image showing infiltration of eosinophil in vitreous body found in Vav2/3$^{ko}$ mouse.
Figure 11:
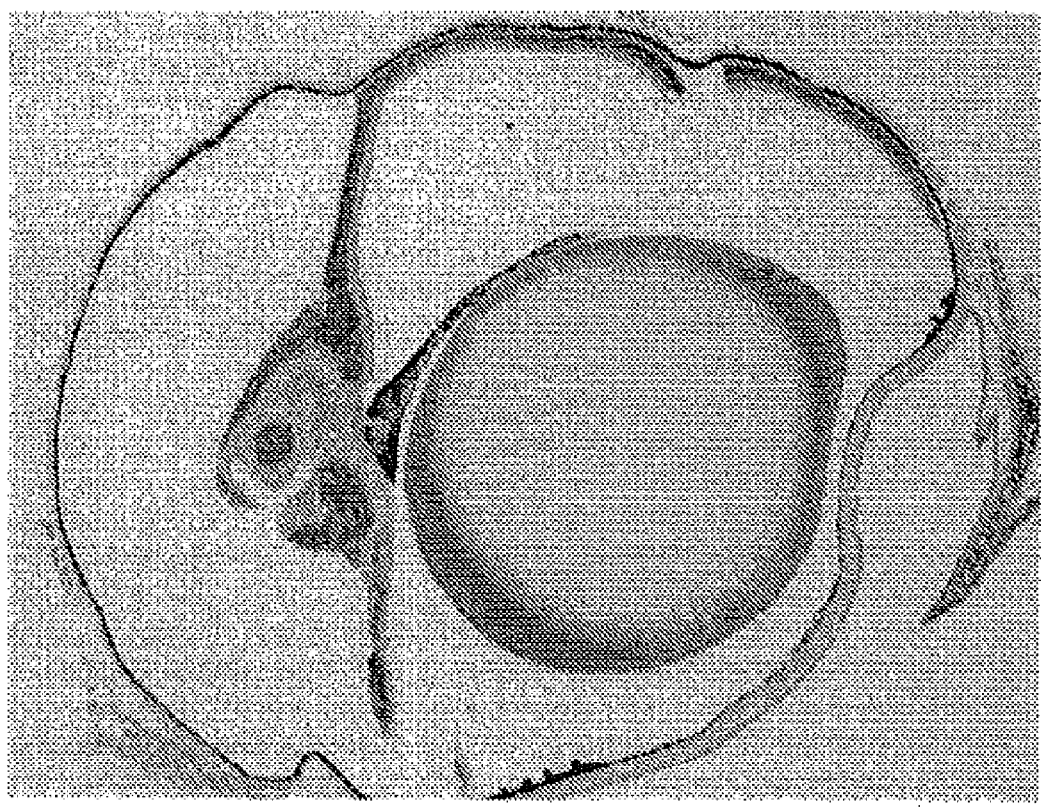
FIG. 11 shows an example showing atrophic degeneration of retina of an eye ball found in Vav2/3$^{ko}$.

Furthermore, Vav2/3$^{ko}$ mice each exhibiting lens degeneration (FIG. 7), cornea thickening and angiogenesis (FIG. 8), vasodilation of an optic nerve (FIG. 9), infiltration of eosinophil in vitreous body (FIG. 10), and atrophic degeneration of retina (FIG. 11) were also confirmed. These are the abnormalities which clinically suggest symptoms of reduced visual acuity, narrowed vision field, damaged vision field, cornea detachment, loss of vision, etc., and therefore occurrence of significant histological changes including degeneration in cornea, iridocorneal angle, lens, retina, vitreous body, optic nerve and the like was confirmed.

Figure 12:
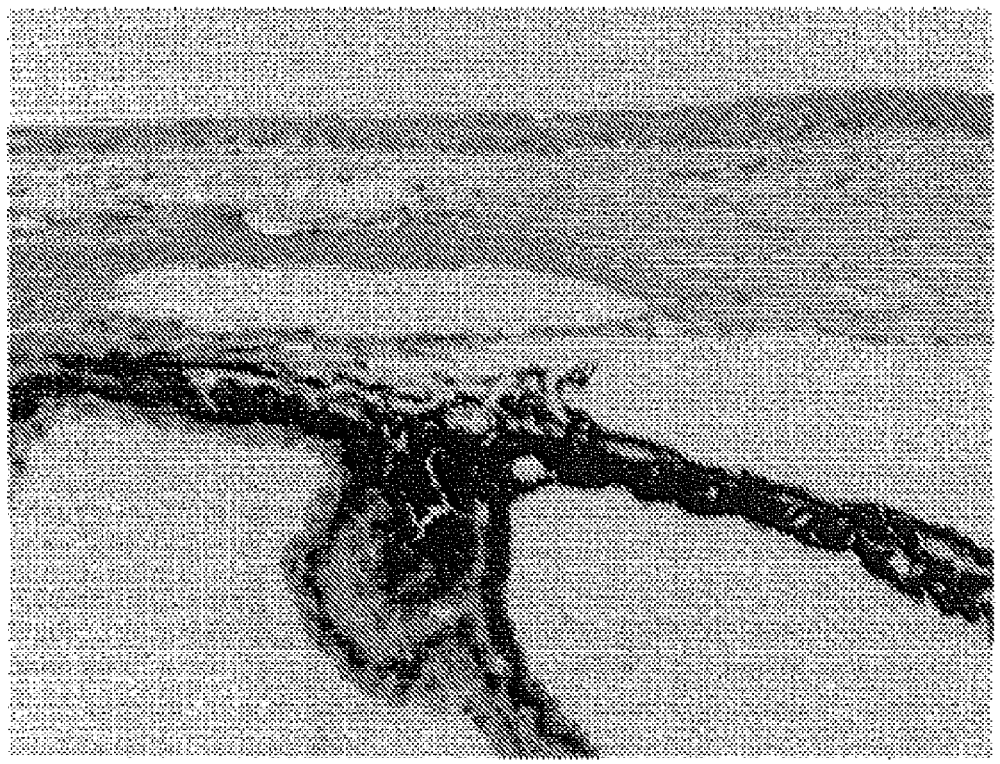
FIG. 12 shows an example showing open iridocorneal angle of an eye ball found in Vav2/3$^{ko}$.

Further, from the six 7-week old Vav2/3$^{ko}$ mice which exhibited very high intraocular pressure when the intraocular pressure was measured six times by using a Tonometer, eye balls were taken out right after the sixth measurement and fixed with 2.5% glutaraldehyde solution (TAAB) for an electron microscope, which had been diluted with a deionized and neutral methanol solution containing 10% formalin, to give a tissue specimen for measuring iridocorneal angle. As a result, two out of six animals showed open iridocorneal angle (FIG. 12).

Example 3

Vav2/3$^{ko}$ mouse of the present invention and wild type C57BL/6 mouse (control) as a background were raised until Week 3, Week 10, Week 15 and Week 30 under the same condition as Example 1. After heavily anaesthetizing the mice with sodium pentobarbital solution, the eye balls were quickly removed and one of them was fixed with 2.5% glutaraldehyde solution (TAAB) for an electron microscope, which had been diluted with a deionized and neutral methanol solution containing 10% formalin, to examine the anterior chamber of the eye. The other eye ball was fixed for 12 hours by using Davidson's solution for observing retina. Fixed tissues were embedded in paraffin solution and cut into a 5 μm piece having cross-section view of an arrow by using a microtome. Then, the piece was de-paraffinized, dehydrated and stained with HE. Results of HE staining are shown in FIG. 13 and FIG. 14.

Figure 13:
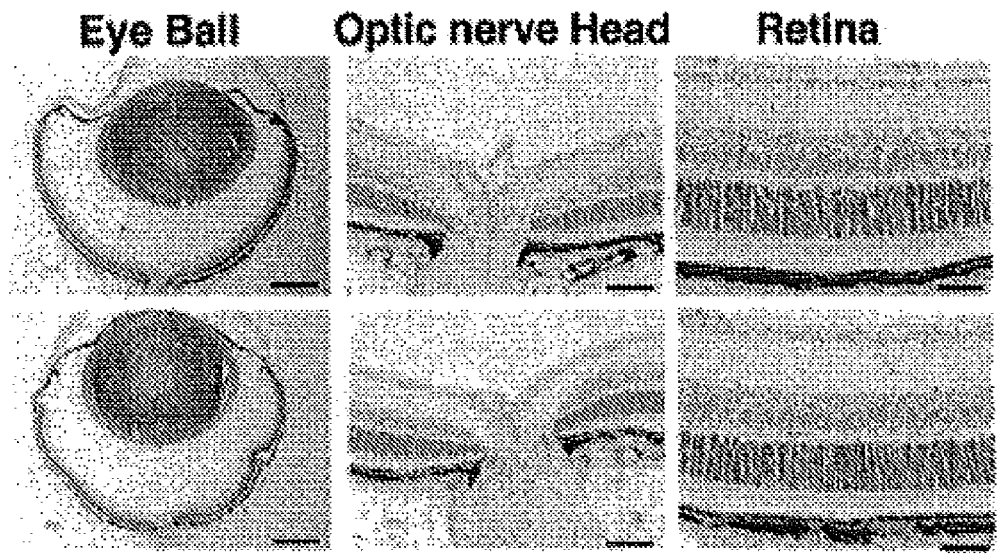
FIG. 13 show photo images showing an eye ball, optic nerve head and retina of a three-week old control mouse (top panel) and Vav2/3$^{ko}$ (bottom panel).
Figure 14:
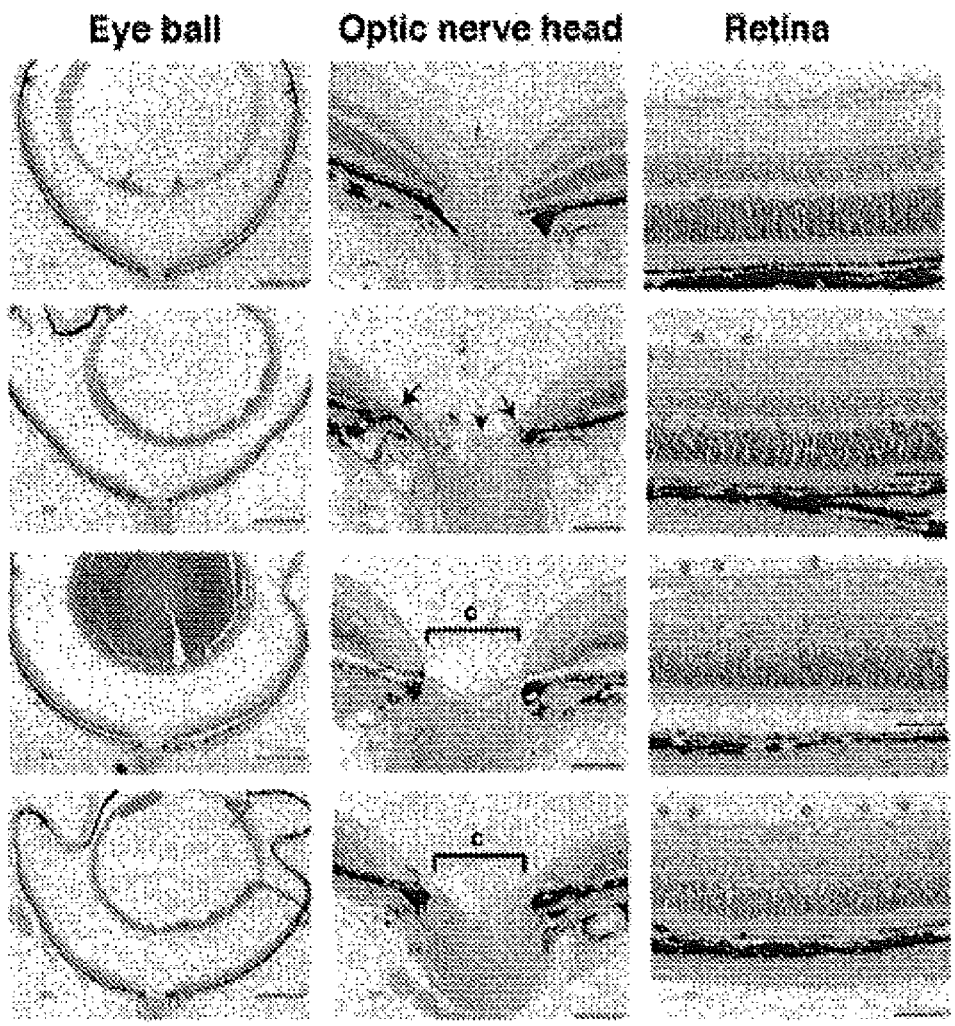
FIG. 14 show photo images showing an eye ball, optic nerve head and retina of a 10-week old control mouse (first panel), 10-week old Vav2/3$^{ko}$ (second panel), 15-week old Vav2/3$^{ko}$ (third panel), and 30-week old Vav2/3$^{ko}$ (fourth panel).

As shown in FIG. 13, from three-week old Vav2/3$^{ko}$ mouse, the optic nerve head appeared to be normal in terms of histology compared to the wild type. Further, no abnormality such as reduced number of optic ganglion cells, etc. was observed. However, once the intraocular pressure starts to increase when Vav2/3$^{ko}$ mouse is 7-week old or over, cupping of the optic nerve head and reduced number of optic ganglion cells were observed for the 10-week old Vav2/3$^{ko}$ mouse, as it is shown in FIG. 14. Furthermore, from the retina of 15-week old or 30-week old Vav2/3$^{ko}$ mouse, even the disruption in optic stratum was found.

Example 4

Figure 15:
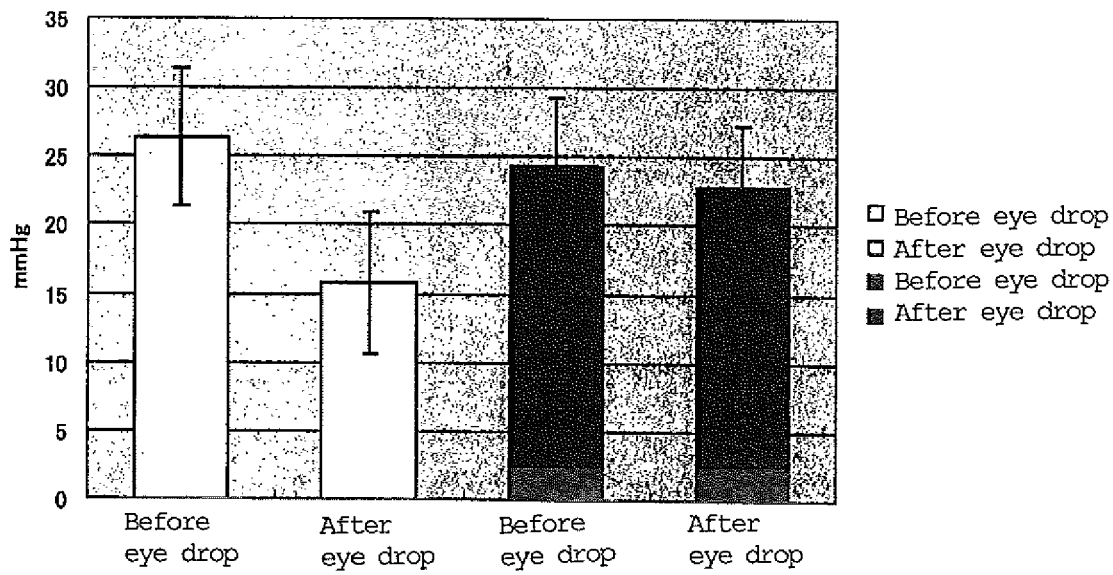
FIG. 15 shows reduction of intraocular pressure when latanoplast had been administered to Vav2/3$^{ko}$. Two bars on the left side correspond to administration of latanoplast while the remaining two bars on the right side correspond to administration of control.

For the 8- to 9-week old Vav2/3$^{ko}$ mouse (No. 12), intraocular pressure was measured between 10 o'clock in the morning and noon by using a Tonometer. Then, 3 μL of latanoplast (0.01%/PBS, manufactured by Cayman Chemical) of a prostaglandin derivative as a therapeutic agent for glaucoma was applied and the intraocular pressure was measured again three hours later. As a control, a group administered only with PBS was prepared at the same time, and analysis was carried out based on Student's t-test (P<0.05). As a result, it was found that the intraocular pressure of the Vav2/3$^{ko}$ mouse was reduced by administration of latanoprost (FIG. 15). Therefore, it was confirmed that the mouse of the present invention is a useful model for evaluation of a therapeutic agent for glaucoma.

Example 5

For the No. 20 animal of each of the 7-week old Vav2/3$^{ko}$ and Vav2$^{ko}$, intraocular pressure was measured between 10 o'clock in the morning and noon by using a Tonometer. Then, 3 μL solution containing 0.02% benzalkonium chloride, 0.5% $NaH_2PO_4$, 0.6% $Na_2HPO_4$, 0.4% sodium chloride and 0.005% Latanoprost (manufactured by Cayman Chemical), or solution having the same composition except that no latanoplast was contained was applied to an eye of the animal based on a blind testing method. Three hours later, the intraocular pressure was measured again. In addition, to Vav2/3$^{ko}$, 3 μL eye-drop solution containing timolol maleate (Trade name; Timoptol, Merck Company, USA, 0.5% solution), or 3 μL eye-drop solution containing dorzolamide hydrochloride (Trade name; Trusopt, Merck Company, USA, 1% solution), both having a different mechanism for reducing intraocular pressure compared to latanoprost, was applied instead of the solution containing latanoprost as described above. Two hours after the application, change in the intraocular pressure was measured.

Figure 16:
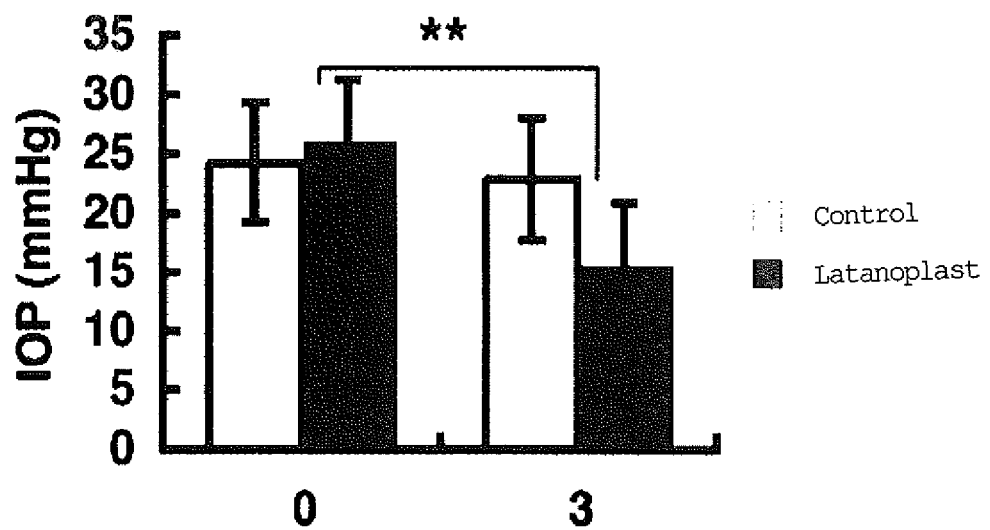
FIG. 16 shows reduction of intraocular pressure when latanoplast or a control solution had been administered to Vav2/3$^{ko}$. Two bars on the left side correspond to the intraocular pressure before the administration while the remaining two bars on the right side correspond to intraocular pressure three hours after the administration.
Figure 17:
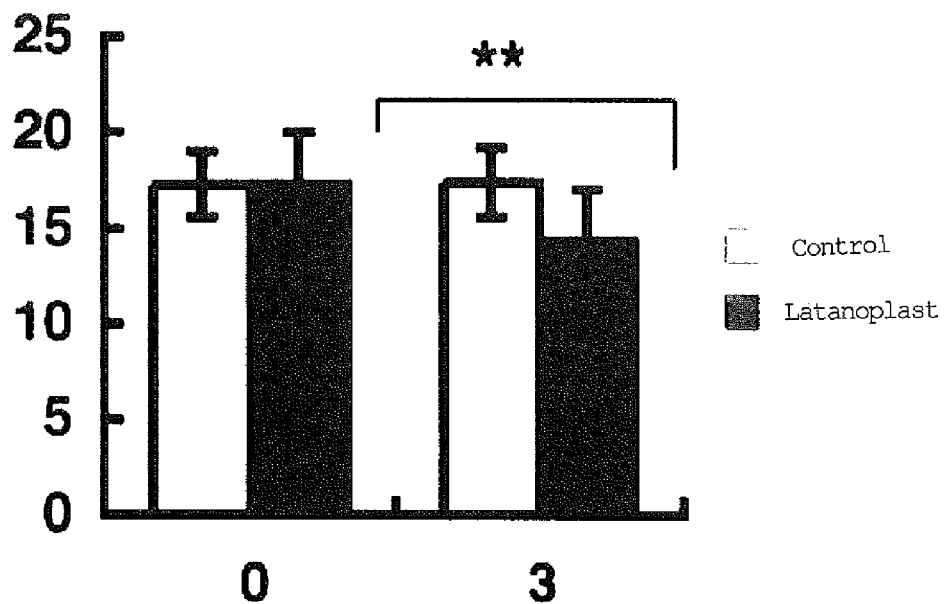
FIG. 17 shows reduction of intraocular pressure when latanoplast or a control solution had been administered to Vav2$^{ko}$. Two bars on the left side correspond to intraocular pressure before the administration while the remaining two bars on the right side correspond to the intraocular pressure three hours after the administration.

As it is indicated in FIG. 16, latanoprost significantly reduced the intraocular pressure of the Vav2/3$^{ko}$ mouse, i.e., from 26.3±5.0 mmHg to 15.8±5.1 mmHg (P<0.01). Furthermore, when the intraocular pressure was again measured twenty four hours after the eye drop administration of latanoprost, it came back to the high value which is the same as the one before the eye drop administration of latanoprost. Similarly, as it is indicated in FIG. 17, latanoprost significantly reduced the intraocular pressure of the Vav2$^{ko}$ mouse, i.e., from 17.4±mmHg to 14.5±mmHg (P<0.01).

Figure 18:
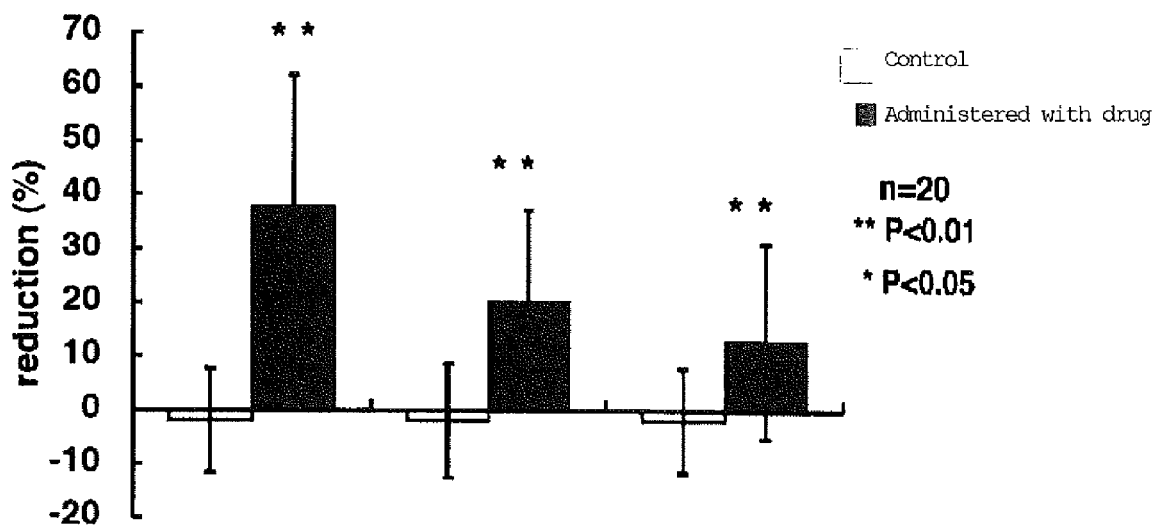
FIG. 18 shows reduction of intraocular pressure when latanoplast, dorzolamide hydrochloride or timolol maleate had been administered to Vav2/3$^{ko}$. Bar on the left side of the graph corresponds to intraocular pressure when latanoplast had been administered, bar at the center of the graph corresponds to intraocular pressure when dorzolamide hydrochloride had been administered, and bar on the right side of the graph corresponds to intraocular pressure when timolol maleate had been administered.

In addition, as it is indicated in FIG. 18, both timolol maleate and dorzolamide hydrochloride have an effect on intraocular pressure of the Vav2/3$^{ko}$ mouse. Ratio of effect on intraocular pressure was 15% and 20% for timolol maleate and dorzolamide hydrochloride, respectively (it was about 40% for latanoprost).

Test Example 1

The eye ball was taken from 10-week old C57BL/6 mouse, and trabecular meshwork, splendor, cilliary body, cornea, retina and lens were isolated and recovered. From each of the tissues, whole RNA was prepared by using TRIzol reagent (Invitrogen Corporation) Then, real time PCR was carried out by using AMV Reverse Transcriptase (Invitrogen Corporation), according to a manual provided for ABi7500 real time PCR instrument (Applied Biosystems INC.). As for a probe for Vav2 and Vav3, Taqman probe (Vav2: Mm00437287, Vav3: Mm00445082) was purchased from Applied Biosystems INC. Further, as a control, Taqman probe for glyceraldehyde triphosphate dehydrogenase (GAPDH, Applied Biosystems INC. Lot No.: 4352339E) was used.

Figure 19:
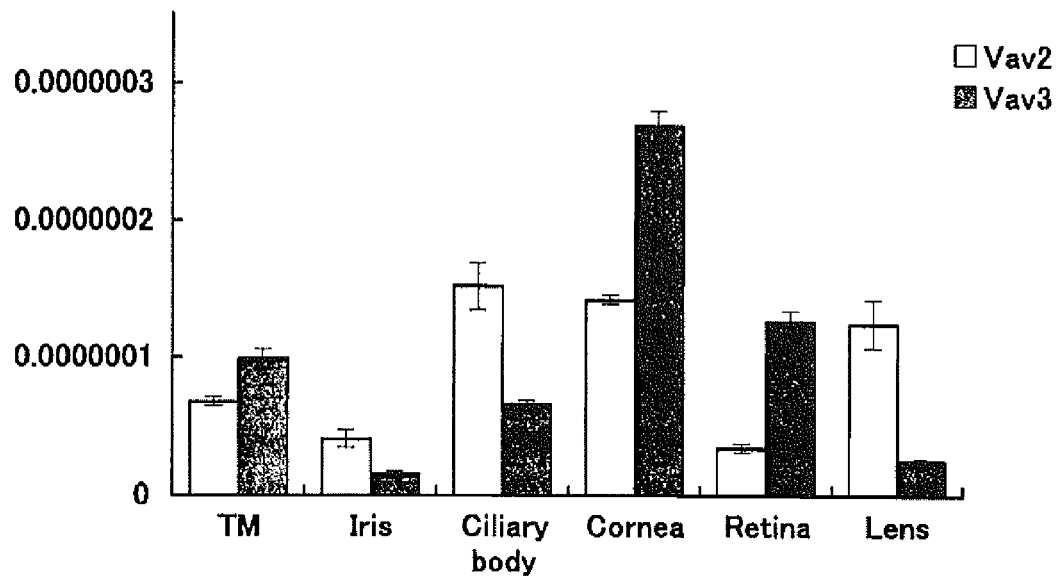
FIG. 19 shows expression of the Vav2 gene and Vav3 gene in each tissue constituting an eye ball of a normal mouse, confirmed by real time PCR.

As a result, it was found that both Vav2 and Vav3 were expressed in each of the above described tissues (FIG. 19).

Test Example 2

The probes consisting of the following nucleotide sequence were chemically synthesized and labeled with [$^{33}$P] dATP.

```
Probe for detection of Vav2:
5'-AGCTGGAGACCGGCTTGAGGCCCTGCTGGTGGTTCGCTCCCGAG
A-3'

Probe for detection of Vav3:
5'-GTTGCCTGTTCTATTACCCCTCTGTCCAGCTGGCTGTTCTGGCT
C-3'
```

The probe for detection of Vav2 includes 45 bases which correspond to the nucleotides from 2275 to 2319 of the Vav2 gene sequence that has been registered with GenBank with accession No. NM_009500. Further, the probe for detection of Vav3 includes 45 bases which correspond to the nucleotides from 2346 to 2302 of the Vav3 gene sequence that has been registered with GenBank with accession No. NM_020505.

The eye ball taken from 10-week old C57BL/6 mouse was frozen, cut into a slice having 20 mm thickness, and placed on top of a slide glass that had been coated with 3-aminopropyltriethoxysilane. Based on the method suggested by Fukaya et al. (Eur. J. Neuroscience, 2005, Vol. 21, pages 1432-1436), the specimen was fixed in 0.1 M sodium phosphate buffer solution containing 4% paraformaldehyde at pH 7.2 for 10 minutes and in 2 mg/mL glycine-phosphate buffered physiological saline at pH 7.2 for 10 minutes, followed by acetylation using 0.1 M triethanolamine hydrochloride containing 0.25% anhydrous acetic acid at pH 8.0. Then, pre-hybridization was carried out for one hour in a buffer solution containing 50% formamide, 50 mM Tris hydrochloride buffer, pH 7.5, 0.02% Ficol, 0.02% polyvinylpyrrolidone, 0.02% BSA, 0.6 M NaCl, 0.25% SDS, 200 mg/mL tRNA, 1 mM EDTA and 10% dextran sulfate. To the resulting mixture, the oligonucleotide which had been labeled with [$^{33}$P]dATP was added (10000 cpm/mL), and then hybridization was carried out at 42° C. for 12 hours. The slide was washed twice at 55° C. for 40 minutes with 0.1×SSC containing 0.1% sarcosine. Consequently, the slide was embedded in Nuclear Track emulsion (NTB-2, Kodak Company) for five weeks and stained with methyl green pyronin.

Figure 20:
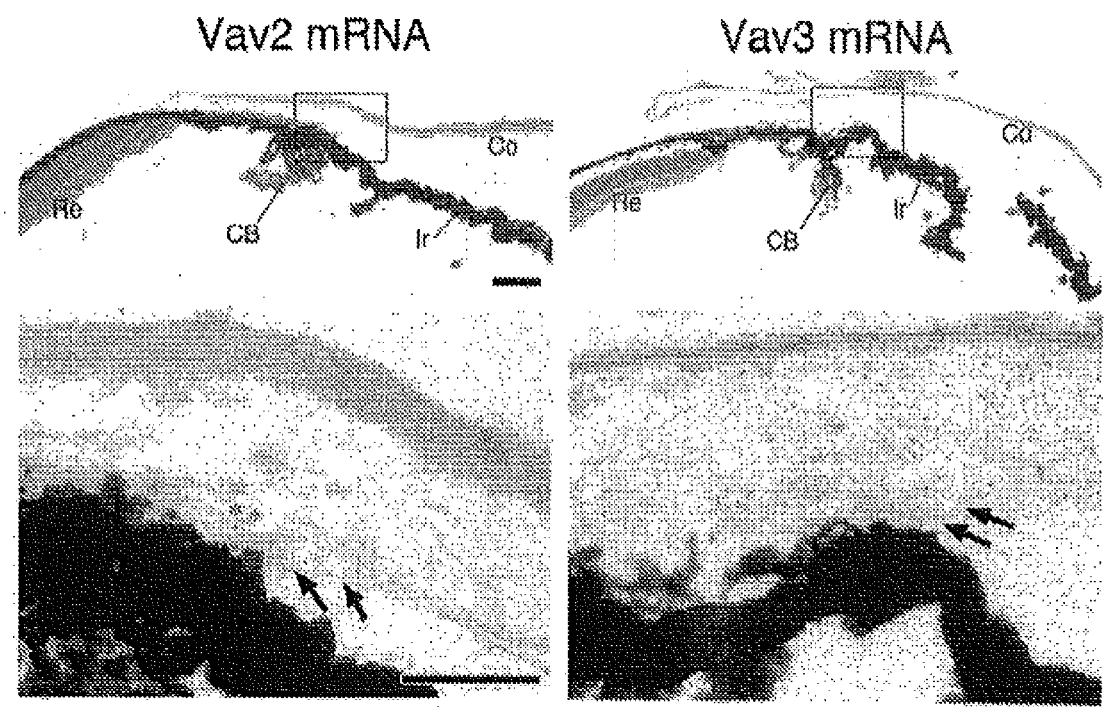
FIG. 20 show photo images obtained by optical microscope which show the expression of the Vav2 gene and Vav3 gene in iridocorneal angle of an anterior chamber of an eye ball of a normal mouse, confirmed by in situ hybridization.

As a result, it was found that both Vav2 and Vav3 were expressed in trabecular meshwork in iridocorneal angle (FIG. 20).

Test Example 3

Figure 21:
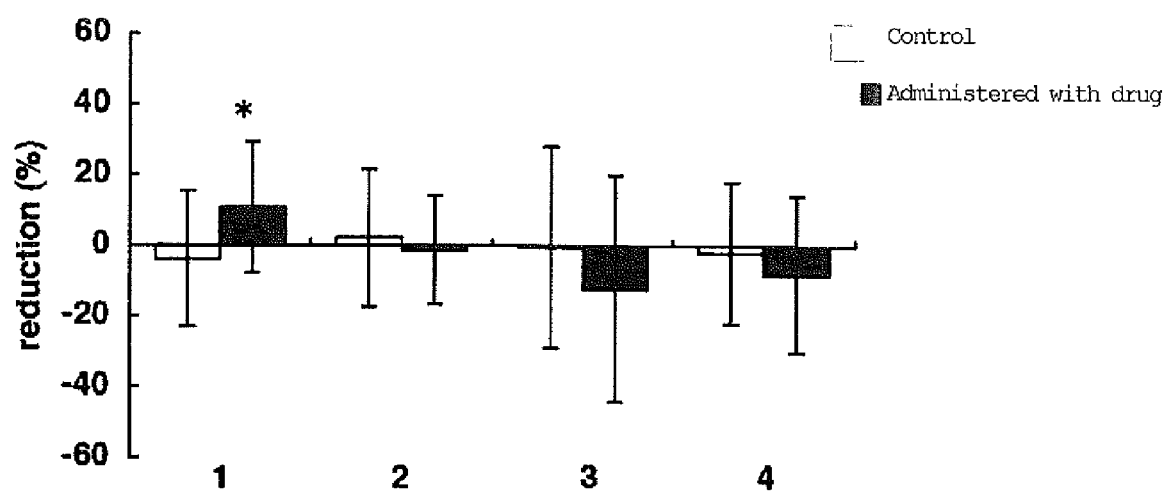
FIG. 21 shows reduction of intraocular pressure when Y-27632 or a control solution had been administered to a control mouse, Vav2/3$^{ko}$, Vav2$^{ko}$, and Vav3$^{ko}$. Bar 1 corresponds to the control mouse, bar 2 corresponds to Vav2/3$^{ko}$, bar 3 corresponds to Vav2$^{ko}$, and bar 4 corresponds to Vav3$^{ko}$.

For No. 20 of each of the 7-week old Vav2/3$^{ko}$, Vav2$^{ko}$ and Vav3$^{ko}$, intraocular pressure was measured between 10 o'clock in the morning and noon by using a Tonometer and then 3 µL of 1 mM/PBS solution of Y-27632 (Calbiochem), which is an inhibitor for Rho-associated protein kinase and has been reported to have an activity of reducing intraocular pressure by acting on an outflow tract for aqueous humor, or 3 µL of PBS solution was applied to an eye. One hour after the administration, the intraocular pressure was measured again. As a result, as it is shown in FIG. 21, Y-27632 did not show any activity of reducing the intraocular pressure for all of the Vav2/3$^{ko}$, Vav2$^{ko}$ and Vav3$^{ko}$ of the present invention.

INDUSTRIAL APPLICABILITY

The non-human animal of the present invention in which the function of Vav2 gene and/or Vav3 gene have/has been impaired can show a naturally occurring eye disease symptom, such as ocular hypertension and/or retinal degeneration, etc., without administering a specific type of drug. As such, it is advantageous in that evaluation of a compound having a therapeutic effect on an eye disease, including a step of administering a test compound to the non-human animal, is not affected by other types of drug that is conventionally administered for artificially inducing an eye disease. In addition, the non-human animal for eye disease model can be importantly used for elucidation of cause or onset mechanism of an eye disease, in particular glaucoma, retinosis, macula degeneration, macula edema and the like which cause retinal degeneration or optic nerve degeneration.

The invention claimed is:

1. A method of screening compounds that treat ocular hypertension or retinal degeneration, comprising the steps of:
   providing a transgenic mouse whose genome comprises a homozygous disruption of a Vav2 and/or Vav3 gene but not a disruption in a Vav1 gene, wherein said mouse has ocular hypertension or retinal degeneration;
   administering a compound to the mouse; and
   evaluating the ocular hypertension or retinal degeneration of the mouse, wherein improved ocular hypertension or retinal degeneration after administering the compound indicates that the compound treats ocular hypertension or retinal degeneration.

2. The method of claim 1, wherein evaluating comprises measuring intraocular pressure in the mouse.

3. The method of claim 1, wherein evaluating comprises performing a pathological test on an ocular tissue of the mouse.

4. The method of claims 1, wherein the compound that treats ocular ocular hypertension or retinal degeneration is a compound that treats glaucoma.

5. The method of claims 1, wherein the compound that treats ocular hypertension or retinal degeneration is a compound that treats eye disease selected from the group consisting of a fundus disease, damaged visual field, open-angle glaucoma, primary closed-angle glaucoma, primary open-angle glaucoma, simple glaucoma, ocular hypertension, ocular hypotension, congenital glaucoma, traumatic glaucoma, hemorrhagic glaucoma, neovascular glaucoma, Posner Schlossman syndrome, steroidal glaucoma, Sturge Weber syndrome, plateau iris malignant glaucoma, closedangle glaucoma due to essential iris atrophy, Chandler's syndrome, absolute glaucoma (disease of a vitreous body), physiological muscae volitantes, detachment of a posterior vitreous body, photopsia, diabetic retinopathy, retinal artery occlusion, retinal vein occlusion, macula degeneration, macula edema and retinopathy of prematurity.

* * * * *